United States Patent
Zheng

(10) Patent No.: US 9,046,878 B2
(45) Date of Patent: Jun. 2, 2015

(54) SYSTEM AND METHOD TO SYNCHRONIZE A PATIENT MONITORING DEVICE WITH A CENTRAL SERVER

(75) Inventor: Chuan Zheng, Bedford, MA (US)

(73) Assignee: Koninklijke Philips N.V., Eindhoven (NL)

( * ) Notice: Subject to any disclaimer, the term of this patent is extended or adjusted under 35 U.S.C. 154(b) by 576 days.

(21) Appl. No.: 13/388,557

(22) PCT Filed: Jul. 9, 2010

(86) PCT No.: PCT/IB2010/053154
§ 371 (c)(1),
(2), (4) Date: Feb. 2, 2012

(87) PCT Pub. No.: WO2011/021115
PCT Pub. Date: Feb. 24, 2011

(65) Prior Publication Data
US 2012/0151093 A1    Jun. 14, 2012

Related U.S. Application Data

(60) Provisional application No. 61/234,335, filed on Aug. 17, 2009.

(51) Int. Cl.
*G04G 7/00*    (2006.01)
*G06F 19/00*   (2011.01)
*H04L 1/16*    (2006.01)
*H04J 3/06*    (2006.01)

(52) U.S. Cl.
CPC .............. *G04G 7/02* (2013.01); *G06F 19/3418* (2013.01); *H04J 3/0664* (2013.01); *H04L 1/1678* (2013.01)

(58) Field of Classification Search
CPC . H04L 1/1678; H04N 21/242; H04N 21/4307
USPC ......................................................... 709/248
See application file for complete search history.

(56) References Cited

U.S. PATENT DOCUMENTS

| 5,566,180 | A    | 10/1996 | Eidson et al. |
| 7,613,210 | B2   | 11/2009 | Takehara |
| 7,627,283 | B2   | 12/2009 | Ratiu et al. |
| 8,308,650 | B2 * | 11/2012 | Bardy ............................ 600/508 |
| 8,369,937 | B2 * | 2/2013  | Bardy ............................ 600/513 |
| 8,396,554 | B2 * | 3/2013  | Miesel et al. ................... 607/19 |
| 8,700,924 | B2 * | 4/2014  | Mian et al. ..................... 713/300 |
| 2004/0167990 | A1 | 8/2004 | Peer |
| 2006/0203855 | A1 | 9/2006 | Senta et al. |
| 2007/0202801 | A1 * | 8/2007 | Frantz .......................... 455/3.05 |
| 2008/0056418 | A1 | 3/2008 | Miki et al. |

(Continued)

FOREIGN PATENT DOCUMENTS

| CN | 100421495 C  | 9/2008 |
| EP | 2075944 A2   | 7/2009 |
| JP | 2001358610 A | 12/2001 |

(Continued)

*Primary Examiner* — Phuoc Nguyen

(57) ABSTRACT

A patient monitoring device (10) transmits patient data packets (70) to a server (12). In response to the server receiving the transmitted patient data packet, the server sends an acknowledgement (ACK) message (72) from the server at the patient monitoring device including a timestamp (74). The patient monitoring device compares the timestamp in the received ACK message with a current time of its clock (28). If the times differ by more than a selected amount, the clock is synchronized to the timestamp.

14 Claims, 4 Drawing Sheets

(56) References Cited

U.S. PATENT DOCUMENTS

| | | |
|---|---|---|
| 2009/0081951 A1 | 3/2009 | Erdmann et al. |
| 2009/0088821 A1* | 4/2009 | Abrahamson .................. 607/60 |
| 2009/0103570 A1 | 4/2009 | Bjorkman |
| 2009/0131762 A1 | 5/2009 | Pelzek et al. |
| 2013/0054839 A1* | 2/2013 | Rodriguez et al. ............ 709/248 |

FOREIGN PATENT DOCUMENTS

| | | |
|---|---|---|
| JP | 2006018375 A | 1/2006 |
| WO | 0188825 A2 | 11/2001 |

* cited by examiner

SYSTEM AND METHOD TO SYNCHRONIZE A PATIENT MONITORING DEVICE WITH A CENTRAL SERVER

CROSS REFERENCE TO RELATED APPLICATIONS

This applications claims the benefit of U.S provisional applications Ser. No. 61/234,335 filed Aug. 17, 2009, which is incorporated herein by reference.

DESCRIPTION

The present application relates to medical monitoring and clinical data devices for monitoring the physiological condition of a patient. It finds particular application in the synchronization of the date and time of patient monitors with a central server and will be described with particular reference thereto.

Presently, as the need for centralized electronic patient records increases, patient records and data are often sent to a centralized server. Typically, patient monitoring devices, which create the patient records and data, include battery powered clocks. As records and data are created, timestamps are included in the record or data file denoting the date and/or time the record or file was created. Often the clocks of patient monitoring devices go long periods of time without being recalibrated. It is not unusual for a clock to gain or lose as much as five minutes or more over the period of a month or so. Incorrect timestamps can alter the apparent time sequence of data entered into the system by a plurality of devices. Errors in the apparent sequence or timing of the events may lead the clinician to the misdiagnose patients or delay the treatment of patients.

Typically, hospitals use a network time protocol (NTP/SNTP) server to synchronize the clocks of the central server to a standardized time. One disadvantage of using a NTP/SNTP server with the patient monitoring devices, is that the monitoring device would need to be connected to the NTP/SNTP server. The connection to the NTP/SNTP server cannot be done with serial/RS232 connections. Another disadvantage with using a NTP/SNTP server is the timing of the synchronization would not be controlled by the patient monitoring device. In some cases, the measurements of the patient monitoring devices may be affected if the NTP/SNTP server tries to synchronize the monitoring device at the same time measurements are being taken.

The present application provides a new and improved method of synchronizing the date and time of patient monitors with a central server which overcomes the above-referenced problems and others.

In accordance with one aspect, a method of synchronizing a patient monitoring device is provided. A patient data packet is transmitted from the patient monitoring device to a server. An acknowledgement (ACK) message is received from the server in response to the server receiving the transmitted patient data packet at the patient monitoring device. A clock of the patient monitoring device is synchronized in accordance with a timestamp in the ACK message.

In accordance with another aspect, a patient monitoring device is provided. A plurality of sensors collect physiological data from a patient. A controller transmits a patient data packet generated from the collected physiological data to a server and receives a acknowledgement (ACK) message from the server in response to receiving the patient data packet. A synchronization unit which synchronizes a clock of the patient monitor to a timestamp of the ACK message.

In accordance with another aspect, a patient monitoring system is provided. A plurality of sensors collects physiological data from a patient. A server transmits acknowledgment (ACK) message in response to receiving a patient data packet, the ACK message having a timestamp. A controller transmits a patient data packet generated from the collected physiological data to the server and receives the ACK message from the server in response to receiving the patient data packet. A synchronization unit which synchronizes a clock of the patient monitor to a timestamp of the ACK message.

One advantage resides in improved efficiency and quality of patient treatment.

Another advantage resides in easier and more reliable synchronization of patient monitoring devices to a common time.

Another advantage resides in control of the timing of the synchronization.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 1 is a diagrammatic illustration of a patient monitoring system in accordance with the present application.

FIG. 2 diagrammatic illustration of a patient monitoring device/central server relationship.

Figure 1:
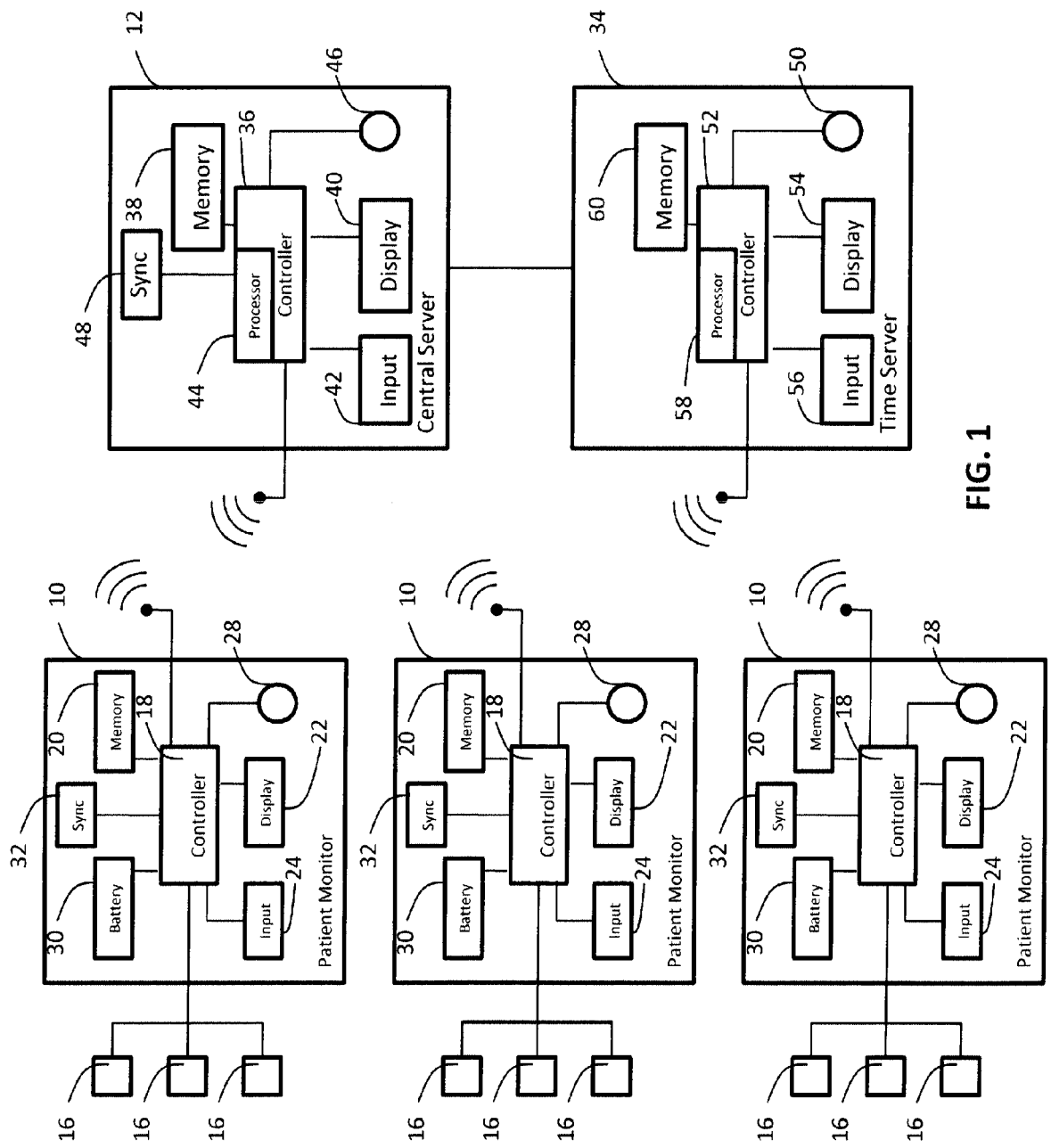

With reference to FIG. 1, a plurality of patient monitors 10 transmit patient data packets to a central server 12. The patient monitors 10, for example may be a patient's bedside monitor, a monitor that travels with the patient, such as a transmitter of an ambulatory patient worn monitoring system, or the like. The patient monitors 10 may also be a more permanent fixture, such as a wall-mounted monitor that is permanently associated with each bed or a room. The patient monitors 10 have one or more sensors 16 that measure physiological parameters of a patient and generate physiological data indicative thereof. These sensors 16 include ECG sensors, IV fluid pumps, blood pressure sensors, SpO2 sensors, pulse sensors, thermometers, respiratory sensors, exhaled gas sensors, and the like. Of course, other sensors 16 can be associated with the patient monitors 10, and not all of the above-mentioned sensors 16 have to be associated with a patient at any given time. As used herein, the sensors 16 signify data sources indicating patient health.

The sensors 16 transmit the generated physiological data via a body coupled network, Bluetooth wires, or the like to a controller 18 of a corresponding patient monitor 10. The patient monitors 10 time stamps the received data and temporarily stores the time stamped data in a memory 20. The controller 18 of the corresponding patient monitor 10 organizes the patient data into packets. The controller 18 transmits the generated patient data packets to the central server 12 via a wireless network, wireless network, a combination of wired and wireless networks, or the like and receives an acknowledgment (ACK) message from the central server 12 acknowledging receiving the patient data packets.

The controllers 18 also control displays 22 of the patient monitors 10 to display the measured physiological data received from each of the sensors 16 in the corresponding patient monitor display 22. The patient monitors 10 also include an input device 24 that allows the user, such as a system administrator, to view, manipulate, and/or interact with the data displayed on the display 22. The input device 24 can be a separate component or integrated into the display 22 such as with a touch screen monitor.

The controller 18 also includes a processor, for example a microprocessor, configured to execute patient monitoring software for performing the operations described in further detail below and time synchronization software. Typically, patient monitoring software is stored in is carried on other tangible memory or a computer readable medium 20 for execution by the processor. Types of computer readable medium 20 include memory such as a hard disk drive, CD-ROM, DVD-ROM and the like. Other implementations of the processor are also contemplated. Display controllers, Application Specific Integrated Circuits (ASICs), and microcontrollers are illustrative examples of other types of component which may be implemented to provide functions of the processor. Embodiments may be implemented using software for execution by a processor, hardware, or some combination thereof.

The patient monitor 10 includes a clock 28 which is controlled by the controller 18. A battery 30 powers the clock, the controller, and the other components of the patient monitor 10. The clock 28 provides the controller with the time and date to be used for time stamping the patient data. The controller 18 also controls the synchronization of the clock 28 of the patient monitor 10 to either the central server 12 or a time server 34. In one embodiment, the patient monitor 10 sends time stamped patient data packets to the central server 12. In response to receiving the patient data packets, the central server 12 transmits an ACK message to the patient monitor 10. The controller 18 may transmit and receive information, dummy patient packets, patient data packets, ACK messages to or from the central server 12 and the time server 34 through means of communication including RS232, HL&LAN, NTP protocol, SNTP protocol, and the like. The ACK message includes a time stamp that is indicative of the time and date of the central server 12 received the corresponding acknowledged data packet. The controller compares the time stamp of the ACK message with the current time of the clock 28 of the patient monitor 10 to determine if the patient monitor clock 28 should be synchronized e.g. if the patient monitor clock 28 and the ACK message timestamp differs by more than 5 seconds, for example. In another embodiment, the patient monitor 10 sends dummy data packets to either the central server 12 or time server 34 periodically to cause the return of an ACK message for synchronizing the patient monitor clock 28 to the central server time. The patient monitor 10 preferably transmits the dummy data packets when the patient monitor turns on or at a predetermined time intervals e.g. every hour. In response to receiving the dummy data packets, the central server 12 or the time server 34 transmit an ACK message to the patient monitor 10 which includes a timestamp of the central server 12 or the time server 28. The time on the clock 28 of the patient monitor 10 is then compared to the timestamp for patient monitor 10 synchronization purposes. In order to prevent the operations of the patient monitor 10 from being affected during synchronization, the controller 18 delays the synchronization of the patient monitor clock 28 until any on-going operation is complete. For example, if a patient record is open, the controller 18 delays synchronization until after the patient record is closed; if a patient measurement is being taken, the controller 18 will delay synchronization until after the measurement is finished, time stamped, and logged into the record; when a patient strip is being printed from the patient monitor 10, the controller 18 delays synchronization until after the printing is complete; and the like.

Optionally, a sync unit 32 controls the synchronization of the patient monitor's clock 28 to either the central server 12 or the time server 34. For example, the sync unit 30 checks the time of the patient monitor 10 against a timestamp of an ACK message transmitted from either the central server 12 or the time server 34. If the difference between the clock of the patient monitor 10 and the timestamp from the central server 12 or the time server 34 is greater than a predetermined amount from the time e.g. 5 seconds, the sync unit 30 synchronizes the patient monitor clock 28 to the timestamp of the central server 12 or the time server 34. The sync unit 30 may include a suitable programmed computer or processor, software applied by the controller processor, or the like.

The communications links between the patient monitors 10 and the central station 12 and the time server 34 may be wireless. If the patient monitor 10 is embodied, for example, in a local monitor mounted on an IV stand or worn, the patient can leave the immediate vicinity, taking the patient monitor 10 along. Wireless communication between the patient monitors 10 and the central station 12 and the time server 34 allows greater mobility for the patient while still being able to communicate the patient data packets. If the patient monitor 10 is embodied in a more permanent fixture, the communications links between the patient monitors 10 and the central station 12 and the time server 34 may be hard lines, such as standard Ethernet network cables.

The central server 12 receives patient data packets from a plurality of patient monitors 10. The central server 12 is frequently centrally located in reference to patient monitors 10, such as a central patient database server for a medical office or clinic, a hospital, a health care network, or the like. The patient monitors 10 transmit the patient data packets to a controller 36 of a central server 12. In response to receiving the patient data packets, the controller 36 generates an ACK message. The controller 36 transmits the generated ACK message to the patient monitor 10 that transmitted the patient data packets. The controller 36 may transmit and receive information, dummy patient packets, patient data packets, ACK messages, rejection messages, or the like to the patient monitors 10 through means of communication including RS232, HL&LAN, NTP protocol, SNTP protocol, and the like. The central server 12 also provides storage in memory 38 for the patient data packets as well as other patient information received from the patient monitors 10. Typically, the data is sorted by patient, but may also be indexed by diagnosis, treatment, or the like to facilitate data mining.

The controller 36 of the central server 12 also control a display 40 of the central server 12 to display the patient information received from the patient monitors 10. The central server 12 also includes an input device 42 that allows the user, such as a system administrator, to view, manipulate, and/or interact with the data displayed on the display 40 or manually synchronize a particular patient monitor 10 or the central server 12. The input device 42 can be a separate component or integrated into the display 30 such as with a touch screen monitor. The memory is also accessible remotely by clinicians to generate reports, performs diagnoses, analyzed for best treatments, and the like.

The controller also includes a processor 44, for example, a microprocessor is configured to execute patient data processing, storage, and retrieval software for performing the operations described in further detail below and, optionally, time synchronization software. Typically, control software is stored in a memory or a computer readable medium 38 and be executed by the processor 44. Types of computer readable medium 38 include memory such as a hard disk drive, CD-ROM, DVD-ROM and the like. Other implementations of the processor 44 are also contemplated. Display controllers, Application Specific Integrated Circuits (ASICs), and microcontrollers are illustrative examples of other types of component which may be implemented to provide functions of the processor 38. Embodiments may be implemented using software for execution by a processor, hardware, or some combination thereof.

A clock 46 is also included in the central server 12 and controlled by the controller 36. The clock 46 tracks the central server's time and date. The clock 46 also supplies the central server's 12 time and date for the timestamps on the ACK messages generated by the central server's controller 36. Optionally, the controller 36 controls the synchronization of the clock 46 of the central server 12 to the time server 34. Optionally, a sync unit 48 controls the synchronization of the central server clock 46 to the time server 34. The sync unit 48 may include a suitable programmed computer or processor, software applied by the processor, or the like.

The time server 34 keeps a reference time for the hospital from a reference clock 50. The time server 34 is frequently centrally located in reference to the central server 12 and patient monitors 14, such as a central time server or the like. The reference clock 50 tracks the hospital's reference time and date. The reference clock 50 in one embodiment is a government maintained standard national or world reference clock used by computers, researchers, and the like. In another embodiment, the reference clock 50 is synchronized with the national or world reference clock using the NTP or SNTP protocol.

In one embodiment, the timer server 34 receives dummy or real data packets from a plurality of patient monitors 10. In response to receiving the data packets, the controller 52 generates an ACK message with a timestamp indicative of the reference time and date tracked by the clock 50. The controller 52 transmits the generated ACK message to the patient monitor 10 that transmitted the patient data packets. The controller 52 may transmit and receive information, dummy patient packets, ACK messages to the central server 12 and patient monitors 10 through means of communication including RS232, HL&LAN, NTP protocol, SNTP protocol, and the like.

The controller 52 of the time server 34 also controls a display 54 of the time server 34 to display hospital time information. The time server 24 also includes an input device 56 that allows the user, such as a system administrator, to view, manipulate, and/or interact with the data displayed on the display 54 or manually synchronize a particular patient monitor 10 or the central server 12. The input device 56 can be a separate component or integrated into the display 54 such as with a touch screen monitor.

The controller also includes a processor 58, for example, a microprocessor is configured to execute time maintenance and synchronization software.

Figure 2:
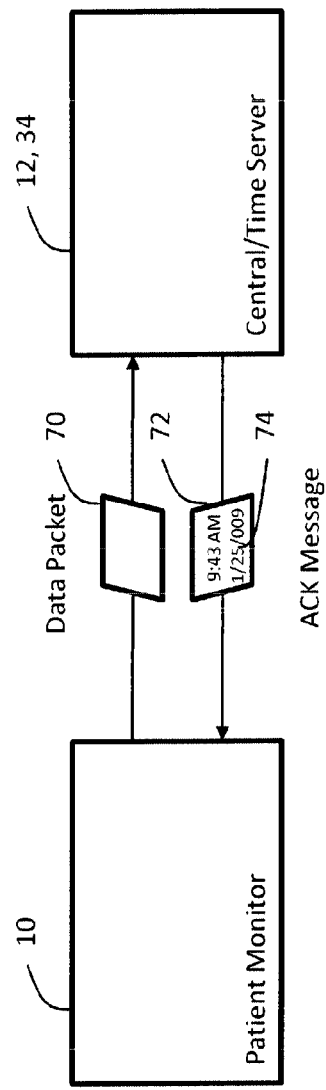

As illustrated in FIG. 2, the patient monitor 10 transmits patient data packets 70 to the central server 12. In response to receiving the patient data packets 70 from a patient monitor 10, the central server 12 transmits an ACK message 72 to the transmitting patient monitor 10 informing the patient monitor 10 that the patient data packet 70 was received by the central server 12. The ACK message 72 includes a timestamp 74 including a sequence of characters indicative of the central 12 server's time and date. In one embodiment, the ACK message 72 is sent even if the patient data packet is rejected by the central server 12. In another embodiment, the patient monitors 10 are synchronized by sending dummy data packets 70 to the central 12 or time server 34. In response to receiving the dummy data packets the central 12 or time 34 servers transmits an ACK message 72 including a timestamp 74 indicative of the central 12 or time 34 server's time and date.

Figure 3:
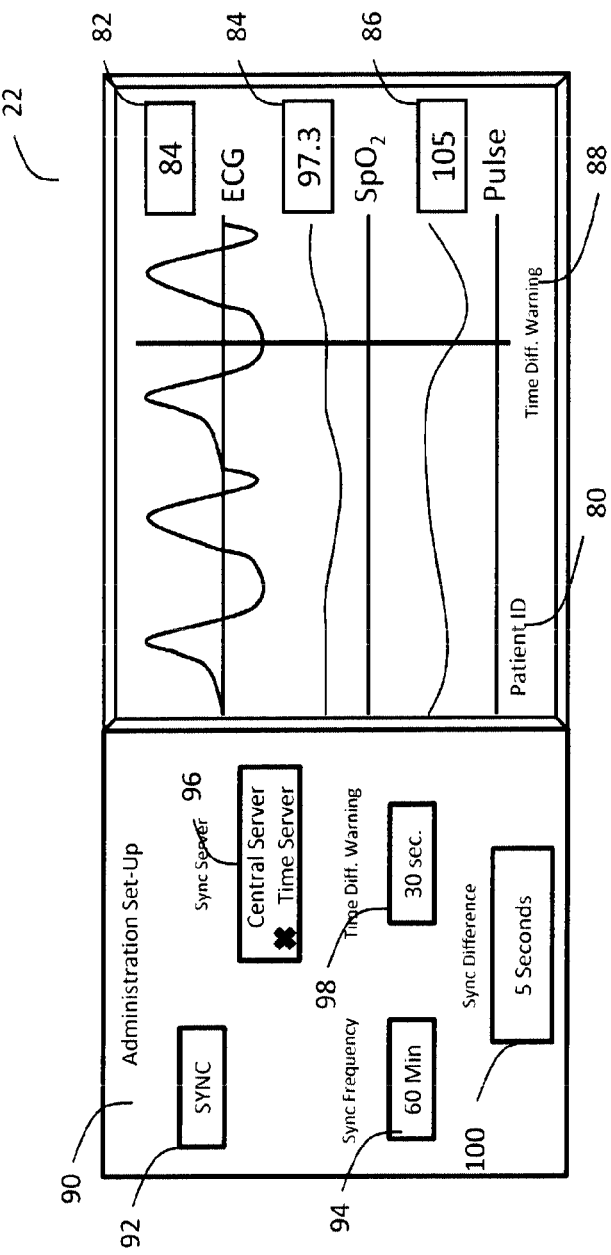
FIG. 3 illustrates an example of a patient monitoring device interface in accordance with the present application.

With reference to FIG. 3, the display 22 of the patient monitor 10 is shown. Physiological data and information of the patient associated with the patient monitor is displayed within the display 22. The display 22 may show a patient ID sub-display 80, an ECG sub-display 82, a SpO2 sub-display 84, a pulse sub-display 86, and the like. The patient monitor 10 includes an alarm to indicate if the change in time of the 10 is greater than a predetermined amount e.g. the patient monitor time changes 30 seconds. In the event that the change in time of the patient monitor 10 is greater than a predetermined amount the alarm activates to warn maintenance and medical personal that the patient monitor 10 may have encountered a timing issue. The alarm includes an audio alarm speaker or a visual alarm 88 e.g. a sync line added to the patient records and sub-displays to indicate that the patient data may have encountered timing issues. In another embodiment, a sync line 88 is added to the patient records and sub-displays at each occurrence of synchronization or a time adjustment greater than the predetermined time.

In one embodiment, a user interface or drop down menu 90 in the display 22 of the patient monitor 10 allows the system administrator to define specific aspects of the synchronization of the patient monitor 10. The interface or menu 90 allows the system administrator to manually sync 92 the time and date of the patient monitor 10. The interface or menu 90 also allows the system administrator to adjust a synchronization time 94 in which the patient monitor 10 periodically transmits a dummy data packet to ensure the patient monitor 10 time and date is accurate. In one embodiment, all of the patient monitors 10 send dummy data packets at the same time to either the central 12 or time 34 server. In another embodiment, the patient monitors 10 send dummy data packets at different time throughout the hour to prevent the central server 12 from being overloaded. In another embodiment, dummy packets are only sent when the time since that the last data transmission exceeds a predetermined condition. Along with the synchronization time 94, the location 96 where the dummy data packet is sent can also be set to prevent the central server 12 from being overloaded with dummy data packets. In one embodiment, the dummy data packets are sent to the central server 12. In another embodiment, the dummy data packets are sent to the time server 34. An alarm 98 or warning is additionally included to indicate if the change in time of the patient monitor 10 is greater than a predetermined amount which can also be determined by the system administrator. The interface or menu 90 also allows the system administrator to adjust the amount of time 100 between the patient monitor clock 28 and timestamp needed to synchronize the patient monitor 10.

Figure 4:
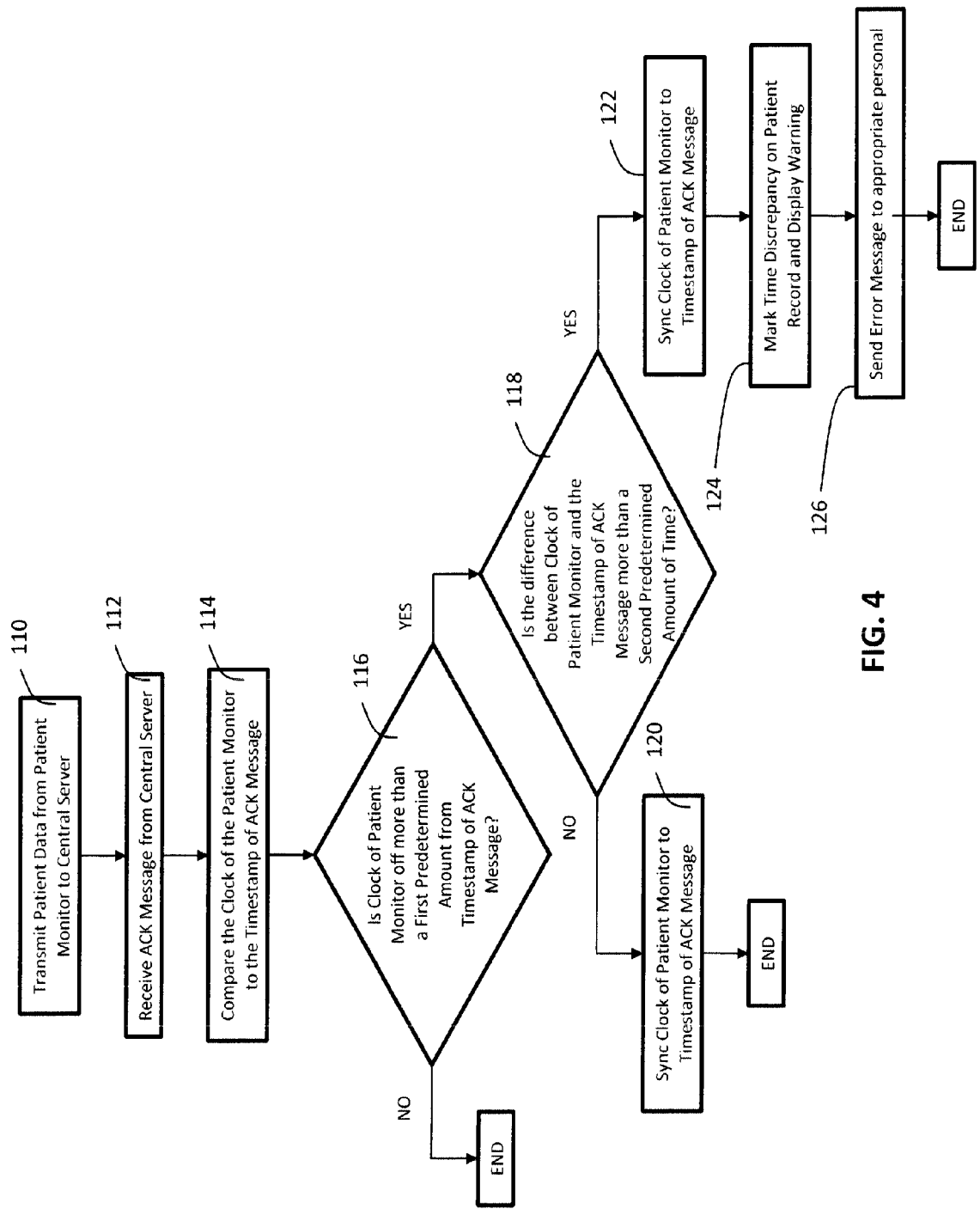
FIG. 4 is a flowchart diagram of the operation of the controller of the patient monitoring device.

With reference to FIG. 4, illustrated is a flowchart diagram of the operation of the controller of the patient monitoring device. At step 110, patient data is transmitted from the patient monitor to central server. At step 112, an ACK message is received by the patient monitor from central server in response to receiving the patient data. At step 114, the clock of the patient monitor is compared to the timestamp of the ACK message. In step 116, it is determined if the clock of the patient monitor is off more than a first predetermined amount from timestamp of ACK message. In response to the patient monitor clock being off more than the first predetermined amount of time from the timestamp of the ACK message, it is determined if the difference between the clock the patient monitor and the timestamp of the ACK message is greater than a second predetermined amount at step 118. If the difference between the clock of the patient monitor and the timestamp of the ACK message is not greater than the second predetermined value the clock of the patient monitor is synced to the timestamp of the ACK message at step 120. If the difference between the clock of the patient monitor and the timestamp of the ACK message is greater than the second predetermined value, the patient monitor is synced to the timestamp of the ACK message at step 122, a time discrepancy and warning is marked on the patient record at step 124, and an error message is sent to appropriate personal at step 126.

Figure 5:
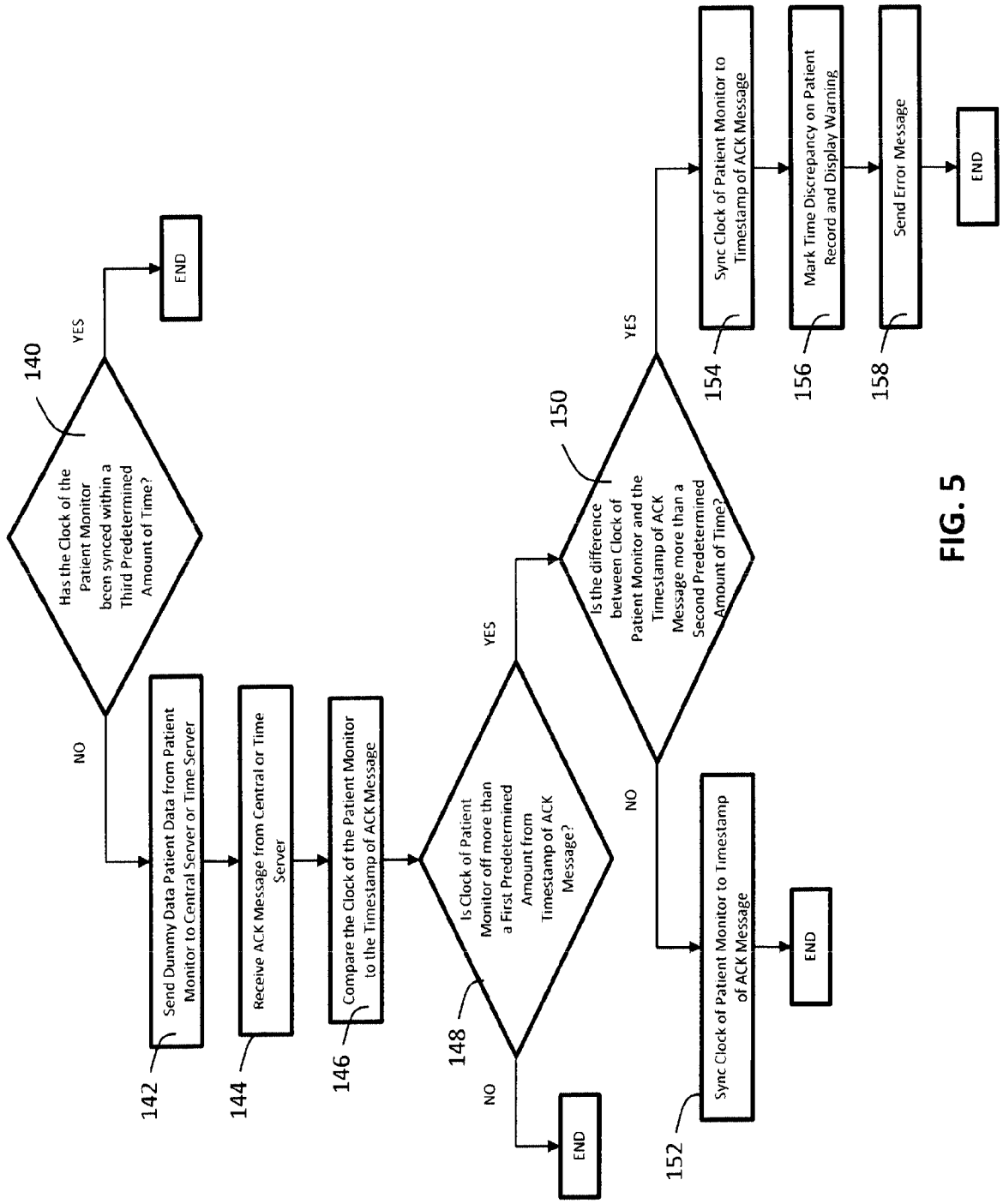
FIG. 5 is a flowchart diagram of the operation of the patient monitoring system in accordance with the present application.

With reference to FIG. 5, illustrated is a flowchart diagram of the operation of the patient monitoring system. At step 140, it is determined is the clock of the patient monitor has been synced within a third predetermined amount of time since the synchronization was last checked. If the clock has not been synced within the third predetermined amount of time, at step 142, dummy patient data is transmitted from the patient monitor to central server or time server. At step 144, an ACK message is received by the patient monitor from central server or time server in response to receiving the patient data. At step 146, the clock of the patient monitor is compared to the timestamp of the ACK message. In step 148, it is determined if the clock of the patient monitor is off more than the first predetermined amount from timestamp of ACK message. In response to the patient monitor clock being off more than the first predetermined amount of time from the timestamp of the ACK message, it is determined if the difference between the clock the patient monitor and the timestamp of the ACK message is greater than the second predetermined amount at step 150. If the difference between the clock of the patient monitor and the timestamp of the ACK message is not greater than the second predetermined value the clock of the patient monitor is synced to the timestamp of the ACK message at step 152. If the difference between the clock of the patient monitor and the timestamp of the ACK message is greater than the second predetermined value, the patient monitor is synced to the timestamp of the ACK message at step 154, a time discrepancy and warning is marked on the patient record at step 156, and an error message is sent to appropriate personal at step 158.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A method of synchronizing a clock of a patient monitoring device with a clock of a central server, the method comprising:
   transmitting a patient data packet from the patient monitoring device to the server;
   receiving at the patient monitoring device an acknowledgement ACK message transmitted by the central server in response to the central server receiving the transmitted patient data packet, the acknowledgement message having a timestamp supplied from the clock of the server indicative of the time and date when the central server received the patient data packet;
   comparing the timestamp of the ACK message with the current time of the clock of the patient monitoring device; and
   if the difference between the current time of the clock of the patient monitoring device and the timestamp of the ACK message is greater than a first predetermined time, synchronizing the clock to the time and date in the timestamp in the ACK message.

2. The method of synchronizing a patient monitoring device according to claim 1, further including:
   generating a sync warning in response to the synchronizing changing the time of the clock more than a second predetermined time.

3. The method of synchronizing a patient monitoring device according to claim 1, further including:
   transmitting a dummy data packet to the central server in response to the clock of the patient monitoring device not having been synchronized within a third predetermined time since the step of comparing was last performed.

4. The method of synchronizing a patient monitoring device according to claim 1, further including:
   delaying synchronization of the patient monitoring device in response to at least one of 1) a patient record being open, 2) patient measurements being taken, 3) patient records being printed or 4) patient data being sent.

5. A non-transitory computer-readable medium carrying software which controls a processor to perform the message according to claim 1.

6. A patient monitoring device comprising:
   a plurality of sensors which sense physiological data about a patient;
   a processor programmed to perform the method according to claim 1.

7. A patient monitoring device comprising:
   a plurality of sensors which are arranged to collect physiological data from a patient;
   a controller which is arranged to:
      transmit a patient data packet generated from the collected physiological data to a central server; and
      receive an acknowledgement (ACK) message transmitted by the central server in response to the central server receiving the patient data packet, the ACK message having a timestamp supplied by a clock of the server indicative of the time and date when the central server received the patient data packet;
   a clock; and
   a synchronization unit which is arranged to synchronize the clock to the date and time in the timestamp of the ACK message if a difference between the timestamp in the ACK message and the clock of the patient monitoring device is greater than a predetermined time.

8. The patient monitoring device according to claim 7, further including:
   a display which is arranged to display a sync warning in response to a time change of the patient monitoring device during synchronization greater than a second predetermined time.

9. The patient monitoring device according to claim 7, wherein the controller transmits a dummy data packet to the central server in response to the clock of the patient monitoring device not having been synchronized within a third predetermined time since the time of the clock of the patient monitoring device was last compared with a timestamp in an ACK message.

10. The patient monitoring device according to claim 7, wherein the controller generates and transmits a data packet indicating that a time change of the clock is greater than a second predetermined amount in response to a difference between the timestamp of the ACK message being greater than a second predetermined time.

11. A patient monitoring system comprising:

a plurality of patient monitoring devices according to claim 7; and a central server which transmits an acknowledgement (ACK) message in response to receiving a patient data packet from a patient monitoring device, the ACK message having a timestamp supplied from a clock of the server indicative of the time and date when the central server received the patient data packet.

12. The patient monitoring system according to claim 11, wherein the server includes:

a patient record memory;

a controller which receives the patient data packet, sends the ACK messages, and stores in the patient record memory patient data from the patient data packets and messages concerning changes in a patient monitoring device's clock time during synchronization.

13. The patient monitoring system according to claim 11, further including:

a time server which periodically adjusts the clock of the central server.

14. A patient monitoring system:

at least one patient monitoring device;

a central server which transmits an acknowledgement (ACK) message in response to receiving a patient data packet from the at least one patient monitoring device, the ACK message having a timestamp supplied from a clock of the central server indicative of the time and date when the central server received the patient data packet;

wherein the at least one patient monitoring device includes:

a controller which is arranged to:

transmit a patient data packet the central server; and receive the ACK message transmitted by the central server in response to the central server receiving the patient data packet; and synchronize a clock of the at least one patient monitoring device to the date and time in the timestamp of the ACK message if a difference between the timestamp in the ACK message and the clock of the at least one patient monitoring device is greater than a predetermined time.

* * * * *